(12) United States Patent
Wiggins et al.

(10) Patent No.: US 8,437,486 B2
(45) Date of Patent: May 7, 2013

(54) CALIBRATED HEARING AID TUNING APPLIANCE

(76) Inventors: Dan Wiggins, Edmonds, WA (US); Donald L Bowie, Burien, WA (US)

( * ) Notice: Subject to any disclaimer, the term of this patent is extended or adjusted under 35 U.S.C. 154(b) by 222 days.

(21) Appl. No.: 12/760,435

(22) Filed: Apr. 14, 2010

(65) Prior Publication Data

US 2010/0290653 A1    Nov. 18, 2010

Related U.S. Application Data

(60) Provisional application No. 61/169,242, filed on Apr. 14, 2009.

(51) Int. Cl.
| H04R 25/02 | (2006.01) |
| H04R 25/04 | (2006.01) |
| H04R 25/00 | (2006.01) |

(52) U.S. Cl.
USPC .............. 381/314; 381/316; 381/320; 381/60

(58) Field of Classification Search .................. 381/314, 381/316, 320, 321, 323, 328, 312, 23.1, 60
See application file for complete search history.

(56) References Cited

U.S. PATENT DOCUMENTS

| 4,548,082 A * | 10/1985 | Engebretson et al. ........... 73/585 |
| 5,197,332 A * | 3/1993 | Shennib ........................... 73/585 |
| 5,210,803 A * | 5/1993 | Martin et al. .................. 381/315 |
| 5,226,086 A * | 7/1993 | Platt ................................. 381/58 |
| 5,604,812 A * | 2/1997 | Meyer ............................. 381/314 |
| 5,608,803 A * | 3/1997 | Magotra et al. ................ 381/314 |
| 5,626,629 A * | 5/1997 | Faltys et al. ...................... 607/57 |
| 5,710,819 A * | 1/1998 | T.o slashed.pholm et al. .............................. 381/316 |
| 5,910,997 A * | 6/1999 | Ishige et al. ................... 381/314 |
| 6,035,050 A * | 3/2000 | Weinfurtner et al. ......... 381/313 |
| 6,058,197 A * | 5/2000 | Delage ........................... 381/314 |
| 6,229,900 B1* | 5/2001 | Leenen ......................... 381/314 |
| 6,366,863 B1* | 4/2002 | Bye et al. ........................ 702/57 |
| 6,424,722 B1* | 7/2002 | Hagen et al. ................... 381/314 |
| 6,574,340 B1* | 6/2003 | Bindner et al. ................. 381/60 |
| 6,674,867 B2* | 1/2004 | Basseas ......................... 381/314 |
| 7,650,005 B2* | 1/2010 | Chalupper .................... 381/320 |
| 7,787,647 B2* | 8/2010 | Hagen et al. ................... 381/314 |
| 7,945,065 B2* | 5/2011 | Menzl et al. ................... 381/314 |
| 8,005,246 B2* | 8/2011 | Ribic ............................. 381/316 |
| 2001/0033664 A1* | 10/2001 | Poux et al. ...................... 381/60 |
| 2005/0069163 A1* | 3/2005 | O'Brien ......................... 381/314 |
| 2005/0196002 A1* | 9/2005 | Hagen et al. ................... 381/314 |
| 2008/0056518 A1* | 3/2008 | Burrows et al. ............... 381/314 |
| 2008/0085023 A1* | 4/2008 | Kulkarni et al. .............. 381/320 |

(Continued)

*Primary Examiner* — Edgardo San Martin
(74) *Attorney, Agent, or Firm* — ÆON Law; Adam L. K. Philipp

(57) ABSTRACT

An calibrated hearing-aid tuning appliance includes a hearing-aid interface for programming settings of a hearing aid worn by a user. The appliance also includes a calibrated audio output subsystem including an audio interface, an audio amplifier, and a calibrated speaker. The audio output subsystem can consistently propagate sound waves having frequency response, sound pressure level, and distortion characteristics within predetermined tolerances. A memory stores pre-recorded sound files and programming instructions for heuristically tuning the hearing-aid. When the programming instructions are communicated to a CPU for execution via a CPU interface, the appliance automatically selects at least one of the pre-recorded sound files; automatically reproduces the selected sound files via the calibrated audio output subsystem; collects feedback from the user based on the sound files thereby reproduced; and automatically adjusts one or more of the settings based on the user's feedback.

12 Claims, 3 Drawing Sheets

U.S. PATENT DOCUMENTS

2010/0303269 A1* 12/2010 Baechler .................. 381/321
2011/0002490 A1* 1/2011 Zukic ..................... 381/314
2011/0051963 A1* 3/2011 Barthel et al. ............. 381/314
2011/0188682 A1* 8/2011 Menzl et al. .............. 381/314
2011/0200214 A1* 8/2011 Knox et al. ............... 381/314

* cited by examiner

CALIBRATED HEARING AID TUNING APPLIANCE

FIELD

The present disclosure relates to hearing aids, and more particularly to a calibrated tuning appliance for tuning hearing aids.

BACKGROUND

At some point in their lives, many people may experience a full or partial decrease in their ability to detect or understand some or all sounds, i.e., a hearing impairment. For many such hard of hearing individuals, the degree of hearing impairment varies by sound frequency. For example, many hard of hearing individuals may have little or no impairment at low sound frequencies, but varying degrees of impairment at higher frequencies. Loss of the ability to understand speech is generally regarded as one of the more detrimental aspects of hearing impairment. The frequency range from about 100 Hz-8 kHz is generally regarded as being the most important for being able to understand speech.

In some cases, certain groups of hard of hearing individuals may share certain general characteristics. For example, statistical thresholds of hearing have been developed for men and women of various ages. However, most individuals have a distinct pattern of impairment that may vary from the statistical thresholds. Consequently, devices that are intended to compensate for an individual's personal hearing impairment often perform better when they are matched to the individual's distinct pattern of impairment.

Many hearing aids include one or more adjustable audio-processing circuits and/or routines. For example, hearing aids commonly include one or more equalization filters and/or amplifiers that may be used to selectively boost or cut various portions of the audible frequency spectrum. In addition, many hearing aids also include other adjustable audio-processing circuits and/or routines, such as gain controls, limiters, compressors, and the like. By adjusting a hearing aid's audio-processing parameters, a hearing aid can often be "tuned" to compensate for an individual's distinct pattern of impairment.

Currently, hearing aids are generally tuned by an auditory healthcare professional, often in a clinical setting. As part of the tuning process, an audiogram (a standardized plot representing the individual's hearing threshold) may be created, generally by performing a "pure tone audiometry" hearing test. Pure tone audiometry hearing tests usually involve presenting pure tones at varying frequencies and levels to an individual wearing calibrated headphones in a sound-controlled environment. The resulting audiogram may provide a starting point for tuning a hearing aid, but it is generally regarded that pure tone audiometry may not accurately measure the full extent of an individual's hearing impairment. For example, pure tone audiometry may not be able to accurately measure the effect of "dead regions" in an individual's basilar membrane. In addition, pure tone audiometry may not measure various factors that are important to speech intelligibility.

Consequently, a further step in tuning a hearing aid generally includes assessing speech intelligibility, often by asking the hearing aid wearer to subjectively evaluate spoken words and/or phrases. Often, the auditory healthcare professional will use his or her own voice as an intelligibility test signal, speaking words or phrases and asking the hearing aid wearer to evaluate the spoken words or phrases. In many cases, the spoken words may include words selected from several pairs of words that differ only by an initial, final, or intervocalic consonant. The auditory healthcare professional may then use the individual's responses to adjust various hearing aid audio-processing parameters.

However, this approach to speech intelligibility tuning may have drawbacks. For example, it may be difficult to achieve consistent results from tuning session to tuning session. In many cases, a hearing aid may need to be tuned multiple times, often over a period of days or weeks, before the wearer finds its performance acceptable. In many cases, the auditory healthcare professional's voice may change slightly or significantly from session to session (e.g., the professional's voice may be altered when he or she has a cold), so it may be difficult compare results from session to session. In other cases, an auditory healthcare professional may retire or move, in which case, subsequent speech intelligibility evaluations may be based on a completely different test signal.

DESCRIPTION

Figure 1:
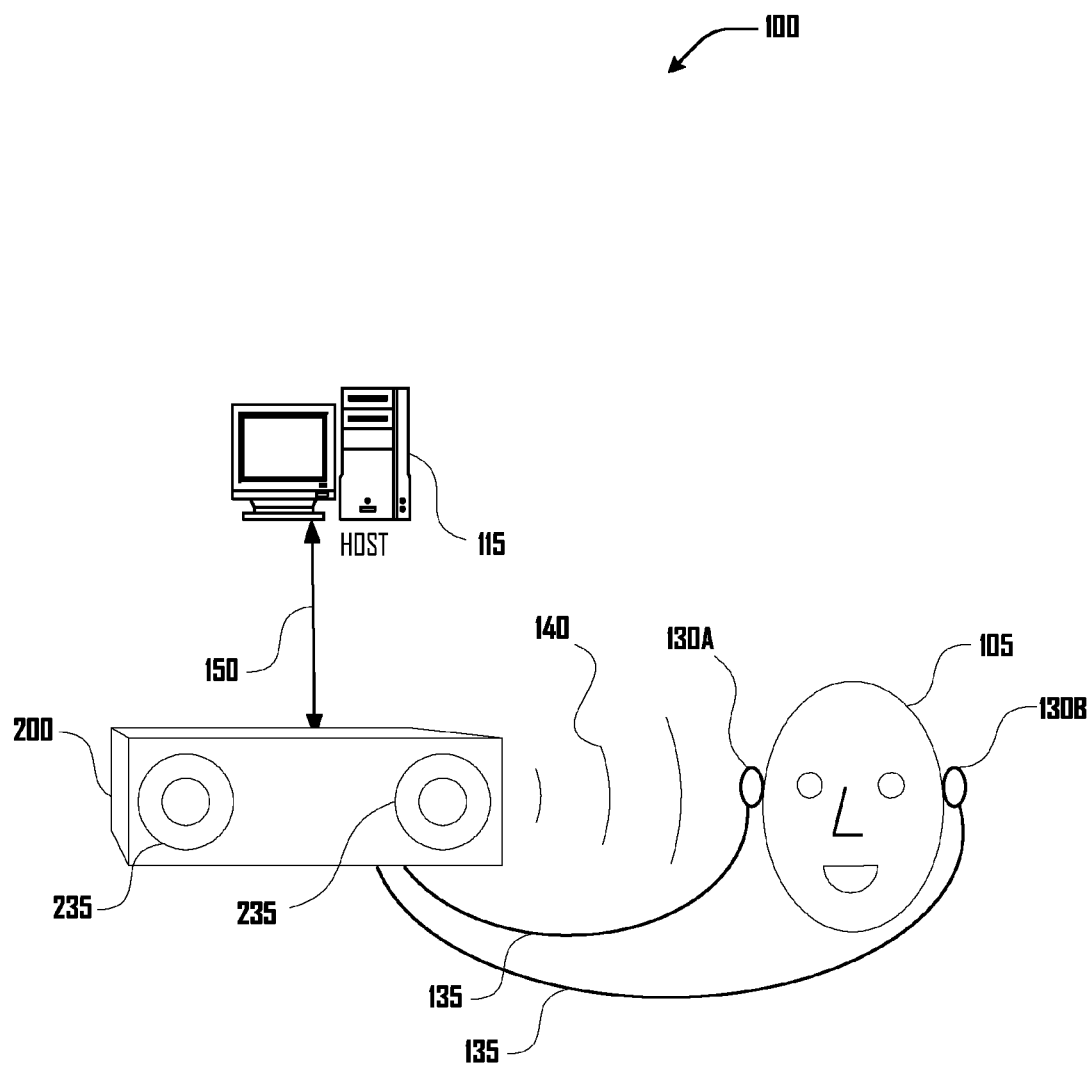
FIG. 1 is a system diagram of a calibrated tuning appliance, a host device, and hearing aids in accordance with one embodiment.

Reference is now made in detail to the description of the embodiments as illustrated in the drawings. While embodiments are described in connection with the drawings and related descriptions, there is no intent to limit the scope to the embodiments disclosed herein. On the contrary, the intent is to cover all alternatives, modifications, and equivalents. In alternate embodiments, additional devices, or combinations of illustrated devices, may be added to, or combined, without limiting the scope to the embodiments disclosed herein.

Various aspects of the illustrative embodiments will be described using terms commonly employed by those skilled in the art to convey the substance of their work to others skilled in the art. However, the embodiments described herein may be practiced with only some of the described aspects. For purposes of explanation, specific numbers, materials, and configurations may be set forth to provide a thorough understanding of the illustrative embodiments. However, the embodiments described herein may be practiced without the specific details. In other instances, well-known features are omitted or simplified in order not to obscure the illustrative embodiments.

Further, various operations and/or communications may be described as multiple discrete operations and/or communications, in turn, in a manner that may be helpful in understanding the embodiments described herein; however, the order of description should not be construed as to imply that these operations and/or communications are necessarily order dependent. In particular, these operations and/or communications need not be performed in the order of presentation.

The phrase "in one embodiment" is used repeatedly. The phrase generally does not refer to the same embodiment; however, it may. The terms "comprising," "having" and "including" are synonymous, unless the context dictates otherwise.

FIG. 1 is a system diagram of a calibrated tuning appliance 200, a host device 115, and hearing aids 130A-B in accordance with one embodiment. Using various embodiments of such a system 100, a hearing aid wearer 105 may be able to tune his or her own hearing aid or hearing aids 130A-B via heuristic tuning routine 285 (see FIG. 2, discussed below) and sound waves 140 produced by calibrated electro-acoustic transducers 235. In one embodiment, calibrated tuning appliance 200 communicates with a host 115, via a host connection 150, and one or more hearing aids 130A-B, via one or more hearing aid connections 135. Although calibrated tuning appliance 200 and its associated tuning routines 285 may be utilized by a hearing aid wearer 105 to tune his or her own hearing aids 130A-B, calibrated tuning appliance 200 may also be utilized by a auditory healthcare professional to provide a consistent tuning experience to one or more hearing aid wearers 105.

In the exemplary embodiment, calibrated tuning appliance 200 comprises a single enclosure, but in other embodiments, calibrated tuning appliance 200 may comprise one or more separate enclosure. For example, in one embodiment, electro-acoustic transducers 235 may be housed in one or more separate enclosures.

In various embodiments, host 115 may comprise a personal computer, laptop, set top box, mobile device, game console, and/or other computing device having a display capability and user-input capability. In alternate embodiments, calibrated tuning appliance 200 may include its own display and/or input device. In still further embodiments, host 115 may comprise a display and/or an input device, but calibrated tuning appliance 200 may use its own internal processor. In some embodiments, calibrated tuning appliance 200 and host 115 may be combined into a single device.

Figure 2:
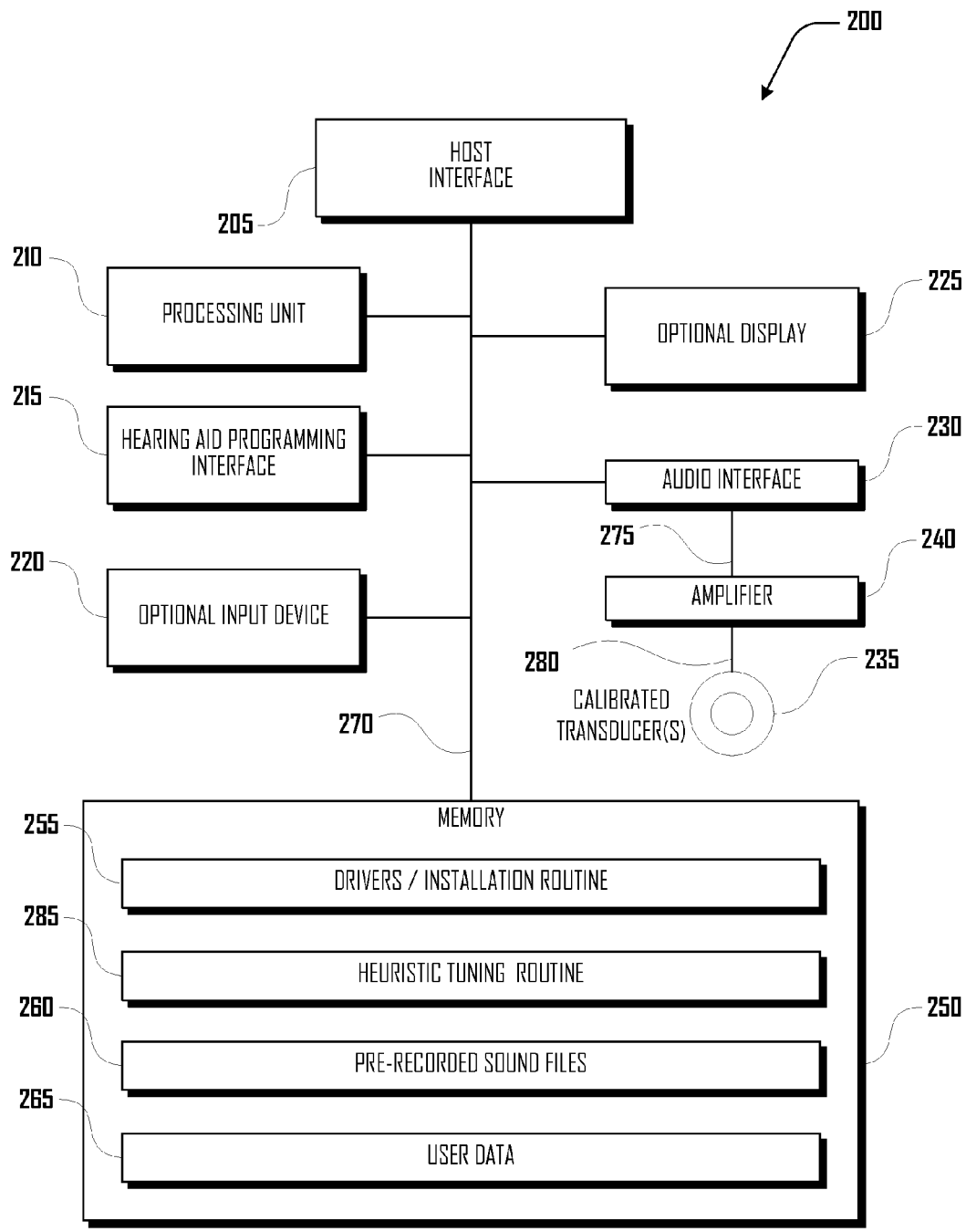
FIG. 2 is a block diagram of a calibrated tuning appliance in accordance with one embodiment.

FIG. 2 illustrates a calibrated tuning appliance 200 in accordance with one embodiment. In one embodiment, calibrated tuning appliance 200 includes a host interface 205, processing unit 210, hearing aid programming interface 215, optional input device 220, optional display 225, an audio interface 230, and a memory 250, all connected to a bus 270.

In one embodiment, host interface 205 comprises a wired serial or parallel data interface, such as Universal Serial Bus ("USB"), IEEE 1394, and the like. In other embodiments, host interface 205 may comprise a wireless data interface, such as an Infrared Data Association ("IrDA") interface, Bluetooth, wireless USB, and the like. In still other embodiments, host interface 205 may comprise a wired or wireless network connection, such as IEEE 802.3 (i.e., Ethernet), IEEE 802.11 (i.e., Wi-Fi), and the like.

In one embodiment, processing unit 210 may comprise a processor sufficient to control communications between host interface 205, memory 250, and audio interface 230 and optional interfaces 220 and 225. In other embodiments, processing unit 210 may comprise a more powerful central processing unit, such as those found in personal computers, laptops, mobile devices, and the like.

In one embodiment, hearing aid programming interface 215 comprises a data interface coupled to calibrated tuning appliance 200 via a fixed or removable coupler, and coupled to one or more hearing aid earpieces 130A-B via a removable coupler. In one embodiment, hearing aid programming interface 215 comprises a wired data connection. In other embodiments, hearing aid programming interface 215 may comprise a wireless data connection. In one embodiment, hearing aid programming interface 215 is coupled to one or more hearing aid earpieces 130A-B via a magnetic-inductive data coupler, as described in co-filed application entitled "MAGNETIC EARPIECE COUPLING SYSTEM," with inventors Daniel Wiggins and Donald Bowie, which is hereby fully incorporated by reference.

Optional input device 220, if present, may include a pointing device, such as a mouse, track pad, track ball, touch screen, and the like. In other embodiments, optional input device 220, if present, may include voice input capacity. Similarly, optional display 225, if present, may include an optical display screen and/or a voice interface.

In various embodiments, memory 250 may comprise volatile random access memory, such as dynamic random access memory; non-volatile memory, such as read-only memory ("ROM") and/or flash memory; non-volatile storage devices, such as a hard disk drive, optical disk, and/or holographic data storage; and/or other memory device. Memory 250 may include internal and/or external memory devices. In one embodiment, memory 250 includes software 255 used to interface with and/or be controlled by a host 115, including one or more device drivers 255 and/or an installation routine.

In one embodiment, drivers/installation routine 255 may include "auto-run" or other automatic installation routines such that in many cases, a hearing aid wearer 105 may be able to initiate a tuning session simply by connecting the calibrated tuning appliance 200 to a host 115. For example, when connected to a host 115, a calibrated tuning appliance 200 may initially identify itself as a common mass storage device, such as a CD-ROM, disk image, flash drive, and the like. Many current operating systems allow such mass storage devices to provide an executable, script, file, or the like that will be automatically opened, launched, and/or executed when a mass storage device mounts and/or is connected. Using such functionality, in one embodiment, calibrated tuning appliance 200 may cause the host 115 operating system to automatically install a device driver to enable the host 115 operating system to interact in a meaningful manner with calibrated tuning appliance 200.

Furthermore, in various embodiments, once host 115 is able to meaningfully interact with calibrated tuning appliance 200, heuristic tuning routine 285 may automatically launch. The operations of heuristic tuning routine 285 are set forth in greater detail in co-pending applications entitled "HEARING AID TUNING METHOD" and "HEURISTIC HEARING AID TUNING SYSTEMS AND METHODS," with inventors Daniel Wiggins and Donald Bowie. Each of the above-referenced applications is hereby fully incorporated by reference.

In some embodiments, heuristic tuning routine 285 may also automatically utilize a network connection on host 115 to provide automatic self-update functionality, such that users may have access to the most recent software version without requiring the user to take any explicit steps to maintain his or her installation of the heuristic tuning routine 285.

In various embodiments, heuristic tuning routine 285 may provide a platform-neutral user interface. For example, in one embodiment, heuristic tuning routine 285 may be implemented as a local or remote web page or web site that provides a user interface via a web browser on host 115. In other embodiments, heuristic tuning routine 285 may be implemented as an interpreted script, interpreted byte code, compiled byte code, virtual machine instructions, and the like. For example, in various embodiments, heuristic tuning routine 285 may be implemented in Java, Flash, and/or other cross-platform development platform. In still further embodiments, heuristic tuning routine 285 may be implemented as one or more conventional single-platform executables.

Thus, in accordance with various embodiments, calibrated tuning appliance 200 may provide an entirely self-contained, "plug and play," solution, in which a user is not required to use or retain a separate software installation disc nor to even download software via the Internet or other data network.

In various embodiments, memory 250 may also include one or more pre-recorded sound files 260. As used herein, the term "sound file" refers to an electronic file containing data from which an audio signal may be constructed. For example, a "sound file" may include pulse-code modulation ("PCM") data, compressed or uncompressed, stored in various file formats, including Audio Interchange File Format ("AIFF"), Waveform audio format ("WAV"), and the like. A sound file may also include lossy compressed audio data, such as audio data encoded in MPEG-1 Audio Layer 3 ("MP3") format, Advanced Audio Coding ("AAC") format, Vorbis format, and the like.

In some embodiments, a sound file may also include data from which an audio signal may be constructed according to one or more synthesis routines. For example, in one embodiment, an audio file may include linear predictive coding ("LPC") coefficients for synthesizing a speech audio signal or other audio signal. An audio file may also include data and/or routines to produce audio signals other than speech, including pure tones, tone combinations, noise, music, and the like.

In one embodiment, some or all pre-recorded sound files 260 may be based on standardized sound files used for subjective evaluation of telecommunication systems, such as sound files prepared in accordance with TIA-920 standard promulgated by the U.S. Telecommunications Industry Association ("TIA"). In some embodiments, pre-recorded sound files 260 may comprise other recordings of speech, including recordings of words, word pairs, phrases, and the like recorded by one or more speakers having determined vocal characteristics (e.g., low male voice, high female voice, and the like). In some embodiments, pre-recorded sound files 260 may further comprise other recorded material, including musical recordings (or excerpts thereof), soundtrack recordings (or excerpts thereof), pure tone recordings, noise recordings (e.g., white noise, pink noise, and other forms of noise having predetermined frequency spectra), and the like.

Memory 250 may also include user data 265. In some embodiments, some or all of memory 250 may be accessible by a user as, for example, a data volume mounted on host 115. In such embodiments, a user may store arbitrary data in memory 250. In other embodiments, a user may not have direct access to memory 250, but heuristic tuning routine 285 may securely store data associated with a user in user data 265. For example, heuristic tuning routine 285 may store in user data 265 user preferences, user hearing aid tuning settings, user hearing aid presets, past user hearing aid tuning settings, and the like. In some embodiments, a user may be able to provide custom-recorded sound files for use with heuristic tuning routine 285, in which case user data 265 may also include one or more custom-recorded sound files. In some such embodiments, calibrated tuning appliance 200 may further comprise a microphone and/or other audio input circuitry.

Audio interface 230 is further connected via an audio bus 275 to amplification circuitry 240 and via at least one amplified audio bus 280, to one or more calibrated electro-acoustic transducers 235. In one embodiment, audio interface 230 comprises a digital-to-analog converter ("DAC"). In other embodiments, a DAC may be included elsewhere in the audio chain, including audio interface 230 through calibrated transducer(s) 235. In various embodiments, amplification circuitry 240, amplified audio bus 280, and one or more calibrated electro-acoustic transducers 235 may be housed in one or more separate enclosures. In one embodiment, amplification circuitry may comprise a Class D (or "switching") amplifier.

In other embodiments, other classes of amplification may be utilized, including Classes A, B, A/B, and the like.

In one embodiment, calibrated tuning appliance 200 may include one or more calibrated electro-acoustic transducers 235 capable of transducing electrical signals into sound waves 140 according to one or more predetermined performance parameters. For example, in one embodiment, electro-acoustic transducers 235 may be capable of producing sound waves from 150 Hz-8 kHz at 85-90 dB (SPL) (measured at 1 meter) with no more than +/−3 dB of deviation in frequency response and no more than 3% total harmonic distortion ("THD"). In one embodiment, a calibrated electro-acoustic transducer 235 may comprise a single wide-range transducer between approximately 1-3 inches in diameter. In other embodiments, a calibrated electro-acoustic transducer 235 may comprise one or more individual transducers of varying sizes. For example, in one embodiment, electro-acoustic transducer 235 may comprise a low-frequency transducer, a high-frequency transducer, and an analog and/or digital frequency-dividing network.

In some embodiments, calibrated tuning appliance 200 may employ analog and/or digital response shaping networks to enable electro-acoustic transducers 235 to meet some or all of the one or more performance parameters. In some embodiments, such analog and/or digital response shaping networks may be incorporated with and/or coupled to audio interface 230, amplification circuitry 240, audio bus 275, amplified audio bus 280, and/or calibrated electro-acoustic transducer 235. In some embodiments, calibrated tuning appliance 200 may also employ analog and/or digital response shaping networks when reproducing a pre-recorded sound file 260 to alter the reproduced frequency spectrum of the audio signal propagating in the air to suit a desired frequency spectrum.

Because electro-acoustic transducers 235 are calibrated to perform to a known standard, in various embodiments, calibrated tuning appliance 200 may be capable of consistently reproducing one or more pre-recorded sound files 260 (and/or custom-recorded sound files) such that propagated sound waves 140 in the air have frequency response, sound pressure level ("SPL"), and distortion characteristics within predetermined tolerances. Thus, different users may have a similar experience when similar sound files 260 are reproduced on different calibrated tuning appliances 200. Similarly, a user's calibrated tuning appliance 200 may provide a consistent tuning standard with little or no variation from tuning session to tuning session, reducing or eliminating inconsistencies such as variations in a human auditory healthcare professional's voice from session to session.

Figure 3:
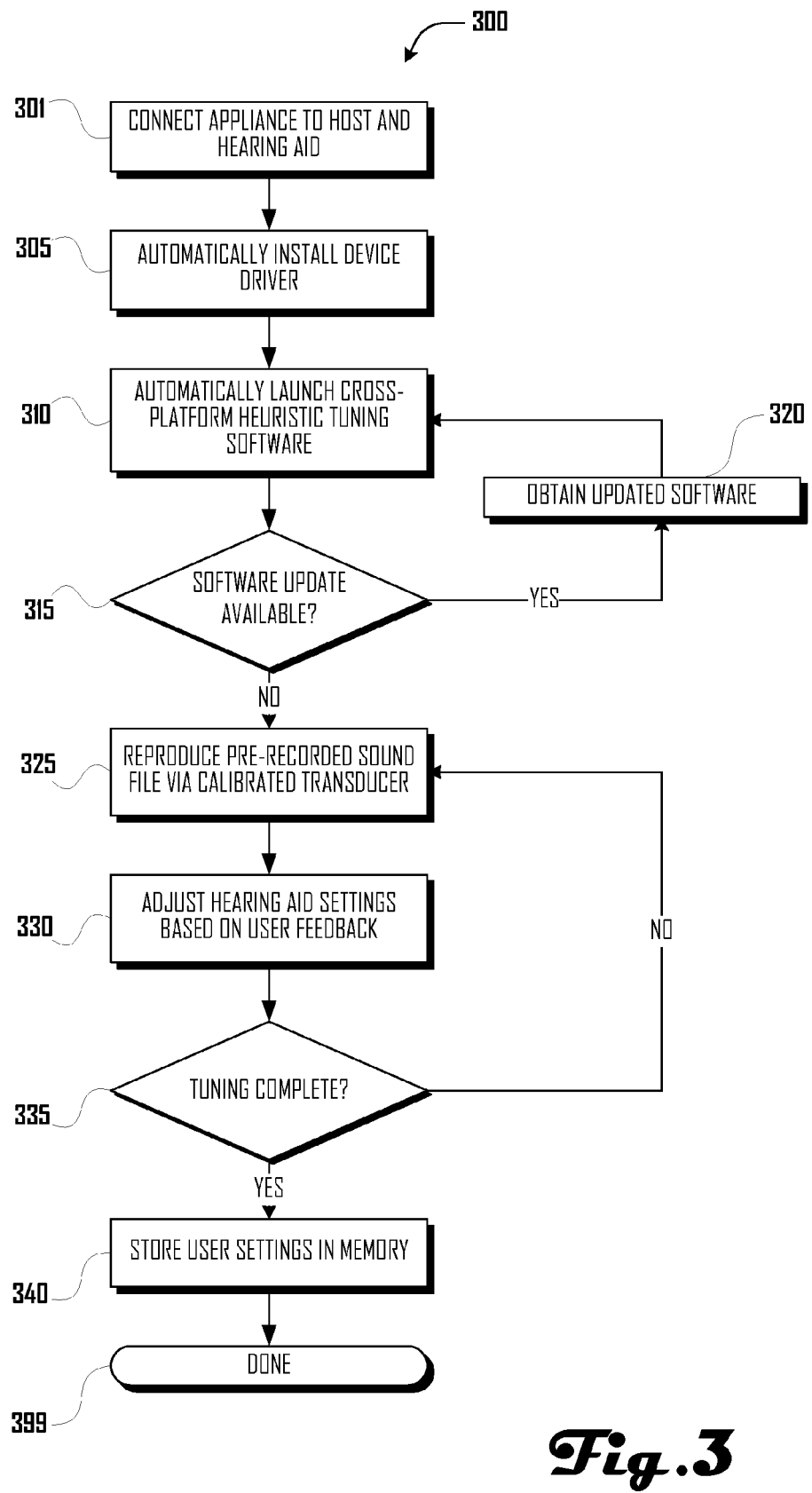
FIG. 3 is a flow diagram illustrating a calibrated tuning appliance tuning routine in accordance with one embodiment.

FIG. 3 is a flow diagram illustrating a calibrated tuning appliance tuning routine 300 in accordance with one embodiment. At block 301, a calibrated tuning appliance 200 is connected to a host 115 and to one or more hearing aids 130A-B. At block 305, a device driver 255 is automatically installed (if needed) at host 115, and at block 310, heuristic tuning routine 285 is automatically launched. At block 315, routine 300 determines whether a software update is available. If so, the updated software is obtained in block 320, stored in memory 250, and the updated heuristic tuning routine 285 is re-launched in block 310. When no more software updates are available, routine 300 proceeds to block 325, one or more pre-recorded sound files are audibly reproduced for the user via calibrated electro-acoustic transducer 235. In block 330, the user's hearing aid settings are adjusted in accordance with feedback obtained from the hearing aid wearer 105. If additional tuning is desired, routine 300 repeats blocks 325-35 until tuning is complete. Once tuning is complete, the final set of hearing aid settings is stored in block 340 in user data 265 in memory 250. Routine 300 ends at block 399.

Although specific embodiments have been illustrated and described herein, it will be appreciated by those of ordinary skill in the art that a whole variety of alternate and/or equivalent implementations may be substituted for the specific embodiments shown and described without departing from the scope of the present invention. This application is intended to cover any adaptations or variations of the embodiments discussed herein.

The invention claimed is:

1. An automated, self-contained calibrated hearing-aid tuning appliance comprising:
   a hearing-aid interface for programmatically coupling with a hearing aid worn by a user, said hearing aid having a plurality of programmatically adjustable settings;
   a calibrated audio output subsystem including:
      an audio interface,
      an audio amplifier, and
      a calibrated electro-acoustic transducer,
   said calibrated audio output subsystem being capable of consistently propagating sound waves having frequency response, sound pressure level, and distortion characteristics within predetermined tolerances;
   a memory storing a plurality of pre-recorded sound files and a plurality of programming instructions for heuristically tuning said hearing-aid; and
   a CPU interface for communicatively coupling with a central processing unit, including communicating said plurality of programming instructions to said central processing unit for execution, the appliance being thereby operative to:
      automatically select at least one of said pre-recorded sound files;
      automatically reproduce said selected at least one of said pre-recorded sound files via said calibrated audio output subsystem;
      collect feedback from said user based on said reproduced at least one of said pre-recorded sound files; and
      automatically programmatically adjust at least one of said plurality of programmatically adjustable settings based at least in part on said collected feedback from said user.

2. The self-contained appliance of claim 1, wherein said CPU interface is configured to communicatively couple with a host computer that hosts said central processing unit, said host computer further providing a display and an input device for collecting said feedback from said user.

3. The self-contained appliance of claim 2, wherein said memory is configured to be accessible by said host computer as a mass storage device when the appliance is coupled with said host computer via said CPU interface.

4. The self-contained appliance of claim 2, wherein said memory further stores a device driver that, when installed on said host computer, enables said host computer to control said hearing-aid interface and said calibrated audio output subsystem via said CPU interface.

5. The self-contained appliance of claim 4, wherein said memory further stores an installation routine configured to automatically install said device driver on said host computer and invoke said plurality of programming instructions when the appliance is coupled with said host computer via said CPU interface.

6. The self-contained appliance of claim 1, wherein said plurality of programming instructions provide a platform-neutral user interface for reproducing said at least one of said pre-recorded sound files and collecting said feedback from said user.

7. The self-contained appliance of claim 1, wherein said calibrated electro-acoustic transducer comprises a wide-range electro-acoustic transducer between approximately one to three inches in diameter.

8. The self-contained appliance of claim 1, wherein said audio amplifier comprises a Class D audio amplifier.

9. A computer-implemented method for automatically tuning a hearing aid worn by a user, the hearing aid having a plurality of programmatically adjustable settings, the method comprising:
   coupling, by the computer, with a self-contained hearing-aid tuning appliance comprising a computer interface, a hearing-aid interface, a memory storing a plurality of pre-recorded sound files and a plurality of programming instructions, and a calibrated audio output subsystem capable of consistently propagating sound waves having frequency response, sound pressure level, and distortion characteristics within predetermined tolerances;
   programmatically coupling, by the computer via said hearing-aid interface, with the hearing aid; and
   executing said plurality of programming instructions by the computer to iteratively perform a heuristic hearing-aid tuning routine, including:
      automatically selecting at least one of said pre-recorded sound files;
      automatically reproducing, by the computer via said calibrated audio output subsystem, said selected at least one of said pre-recorded sound files;
      collecting feedback, by the computer, from the user based on said reproduced at least one of said pre-recorded sound files; and
      automatically programmatically adjusting, by the computer, at least one of the plurality of programmatically adjustable settings based at least in part on said collected feedback from said user.

10. The method of claim 9, further comprising automatically mounting, by the computer, said memory as a mass storage device upon coupling with said hearing-aid tuning appliance.

11. The method of claim 10, further comprising automatically installing, by the computer, a device driver upon coupling with said hearing-aid tuning appliance, said installed device driver enabling the computer to control said hearing-aid interface and said calibrated audio output subsystem.

12. A system for automatically tuning a hearing aid worn by a user, the hearing aid having a plurality of programmatically adjustable settings, the system comprising:
   a self-contained hearing-aid tuning appliance comprising a host-computer interface, a hearing-aid interface, a memory storing a plurality of pre-recorded sound files and a plurality of programming instructions, and a calibrated audio output subsystem capable of consistently propagating sound waves having frequency response, sound pressure level, and distortion characteristics within predetermined tolerances;
   a host computer comprising a central processing unit coupled with said hearing-aid tuning appliance and operative to execute said plurality of programming instructions to iteratively perform a heuristic hearing-aid tuning routine, including:
      automatically selecting at least one of said pre-recorded sound files;

automatically reproducing said selected at least one of said pre-recorded sound files via said calibrated audio output subsystem;

collecting feedback from the user based on said reproduced at least one of said pre-recorded sound files; and automatically programmatically adjusting at least one of the plurality of programmatically adjustable settings based at least in part on said collected feedback from said user.

* * * * *